United States Patent [19]

Hodgson et al.

[11] Patent Number: 4,556,050
[45] Date of Patent: Dec. 3, 1985

[54] ARTIFICIAL SPHINCTER INCLUDING A SHAPE MEMORY MEMBER

[76] Inventors: Darel E. Hodgson, 170 Parkside Dr., Palo Alto, Calif. 94306; John F. Krumme, 87 Upenuf Rd., Woodside, Calif. 94062

[21] Appl. No.: 606,408

[22] Filed: May 2, 1984

[51] Int. Cl.⁴ .............................................. A61B 5/00
[52] U.S. Cl. ............................ 128/1 R; 128/DIG. 25; 60/527
[58] Field of Search ............... 128/DIG. 25, 1 R, 346; 251/4, 7, 9, 10, 11, 368; 60/527, 528

[56] References Cited

U.S. PATENT DOCUMENTS

| 3,730,186 | 5/1973 | Edmonds et al. | 128/DIG. 25 |
| 3,890,977 | 6/1975 | Wilson | 128/419 P |
| 3,903,894 | 9/1975 | Rosez et al. | 128/DIG. 25 |
| 4,434,618 | 3/1984 | Dillon | 60/528 |
| 4,489,725 | 12/1984 | Casey et al. | 128/346 |
| 4,490,975 | 1/1985 | Yaeger et al. | 60/527 |
| 4,512,338 | 4/1985 | Balko et al. | 128/1 R |

FOREIGN PATENT DOCUMENTS 2251302 6/1975 France ..................... 128/DIG. 25

Primary Examiner—Edward M. Coven
Attorney, Agent, or Firm—Howard L. Rose

[57] ABSTRACT

An artificial sphincter includes an implantable clamp which selectively pinches closed or opens a vessel in a living body. The clamp includes a spring member and a shape memory member that has a memory configuration. Either the vessel opening operation or vessel closing operation is effected by deforming the shape memory member from the memory configuration thereof, the other operation being effected by heat recovering the shape memory member to the memory configuration thereof. The shape memory member is heated by means of an AC source external to the body, the source inducing a heat-generating current, via a coil, in the shape memory member or in a resistive heater element which transfers heat to the shape memory element. The coil is preferably positioned near the surface of the body and is connected with leads to the shape memory member or resistive heater element which may be at a distance form the body surface. The clamp further includes a spongy inner layer which cushions the vessel and distributes the forces thereagainst.

30 Claims, 6 Drawing Figures

ARTIFICIAL SPHINCTER INCLUDING A SHAPE MEMORY MEMBER

FIELD OF THE INVENTION

The present invention relates to the field of controlling the flow of substances through a vessel in a living body. More specifically, the invention relates to artificial sphincters.

BACKGROUND OF THE INVENTION

A sphincter is a muscle that surrounds an opening, tube, or other vesel and serves to selectively close such a vessel. Sphincters are commonly associated with the bladder and urinary system, stomach entrances, and the anus. In each instance, the sphincter selectively opens and closes the vessel to respectively enable or inhibit the flow of a particular substance therethrough.

When the sphincter fails to operate, the art teaches various techniques for artificially performing the functions of the sphincter. Goldstein in U.S. Pat. No. 4,053,952, teaches the use of magnetism to control the flow of fluids. Reincke, in the U.S. Pat. Nos. 4,167,952 and 4,197,835 discloses a fluid inflatable cuff employed in a sphincter application.

In selectively opening and closing a vessel, a number of features appear desirable in an artificial sphincter should be capable of repetitive and controllable operation. That is, the vessel should be selectively opened and closed on demand. Second, the artificial sphincter should be implantable and hence body compatible. Third, it may also be desired to actuate the artificial sphincter remotely, or noninvasively, without the use of wires or the like. Fourth, it would also appear desirable to provide an artificial sphincter having minimal implanted parts and no fluids contained by the implant which would require leak-proofing, proper fluid selection, and/or other safety measures. Fifth, it would further appear desirable to provide an easily operated, reliable mechanism. Sixth, it would still further appear desirable to selectively open and close a vessel without a valve which requires proper seating and relative movement of parts.

SUMMARY OF THE INVENTION

It is an object of the invention to provide an artificial sphincter which includes the above-noted desired features.

In accordance with the invention, an artificial sphincter includes an implantable shape memory member. The shape memory member has a memory configuration to which the shape memory member recovers when heated to recovery temperatures. Operating in concert with the shape memory member is a spring member. At temperatures below recovery, the shape memory member is deformed by the spring member. At recovery temperatures, a deformed shape memory member recovers to the memory configuration thereof. According to the invention, recovery of the shape memory member to the memory configuration can effectuate either the opening or pinching closed of a vessel in a living human (or animal) body, the complementary operation being effectuated by the deforming of the shape memory member. Hence, by selectively applying or withdrawing recovery heat to the shape memory member, the vessel is selectively opened or pinched closed. by means of a remote AC source. The AC source induces current in a coil that transfers current to the shape memory member or in a resistive heater element which transfers heat thereto. The coil is tuned to a desired frequency to avoid interference and may be positioned near the body surface to facilitate AC input when the clamp must be located at a distance from the body surface. The deforming and recovery of the shape memory member is thereby achieved noninvasively and without the need for any wire leads through the skin or implanted power sources.

Further, because the artificial sphincter according to the invention selectively pinches a vessel closed depending on the configuration of a shape memory member, only few elements and no fluid actuation mechanisms are required.

Also, in accordance with the invention, a spongy layer is preferably interposed between the shape memory member and the vessel in order to cushion and protect the vessel and distribute forces thereagainst as the vessel is pinched closed.

In one specific embodiment, the present artificial sphincter comprises a multilayer structure which is coiled about the vessel. In another embodiment, the artificial sphincter comprises a multilayer structure having a horseshoe shape. In each embodiment, the multilayer structure preferably includes at least a shape memory layer, a resilient layer, and an inner surface which presses inwardly against or withdraws from the vessel as the shape memory layer is altered in configuration. Also, in each case, the multilayer structure may alternatively comprise flat layers stacked in a sandwich fashion or coaxial layers.

Preferably, the shape memory member comprises NiTinol, which has been found in the art to be compatible with the human body.

In addition, the spring member resilience may be selected to provide a desired pressure against vessel tissue upon closure of the vessel responsive to deformation of the shape memory member by the springy member. By employing a shape memory member to counteract the springy member, the pressure may be relatively precisely controlled.

BRIEF DESCRIPTION OF THE DRAWINGS

FIG. I is an upper right perspective illustration of one embodiment of a clamp employed in an artificial sphincter according to the invention.

FIGS. II and III are illustrations of an embodiment of an artificial sphincter according to the invention. FIG. II shows the clamp of the artificial sphincter pinching a vessel closed; FIG. III shows the clamp of the artificial sphincter dimensioned to permit flow through the vessel.

Figure 1:
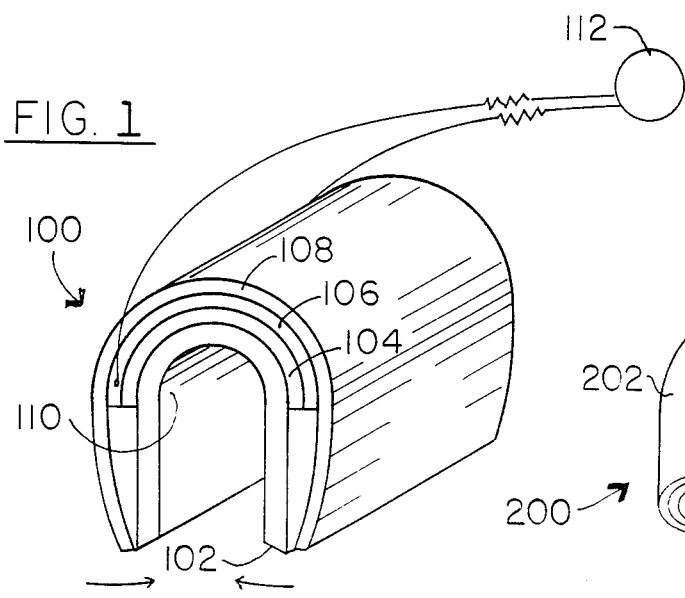
Figure 2:
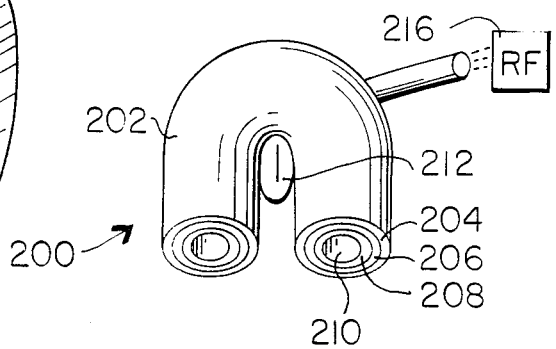
Figure 3:
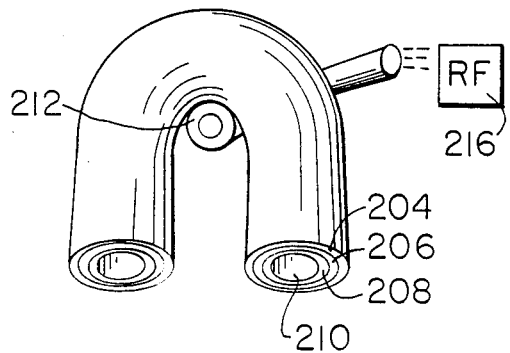
Figure 4:
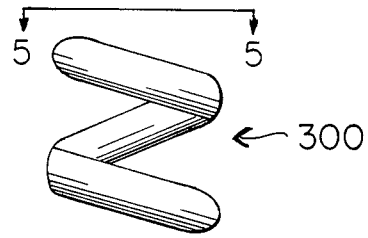
Figure 5:
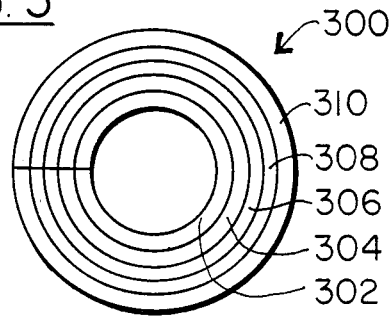
Figure 6:
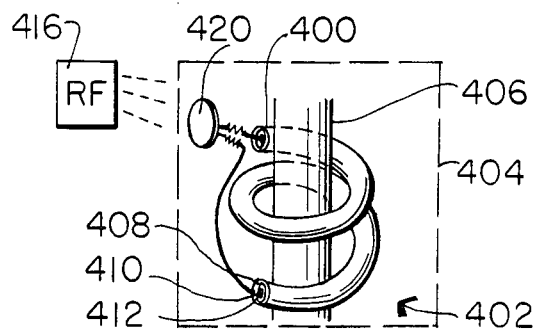

FIG. IV is a front view illustration of a coil-shaped clamp employed in an artificial sphincter according to the invention.

FIG. V is a top view illustration of FIG. IV.

FIG. VI is an illustration of a coil-shaped clamp with coaxial layers employed in an artificial sphincter according to the invention.

DESCRIPTION OF THE INVENTION

In FIG. I, a clamp 100 is shown as an implantable multilayer structure having a horseshoe shape. The clamp 100 includes—passing from the inner layer to the outer layer—a spongy inner layer 102, a shape memory layer 104, a resistive heater layer 106, and a spring member layer 108. The inner surface of the spongy inner layer 102 defines the inner surface 110 of the clamp 100. An AC pickup coil 112, connected to provide current to the heater layer 106, is positionable close to the body surface to receive AC input. The coil 112 is preferably tuned to a desired frequency.

The springy member layer 108 as shown applies an inward pressure—as shown by the arrows—on the clamp 100 urging the clamp 100 to contract. The inward pressure of the springy member layer 108 urges the other layers 102 through 106 to be deformed to reduce the dimensions of the longitudinally extending channel bounded by the inner surface 110. Of particular significance, the springy member layer 108 urges the shape memory member layer 104 to deform from a memory configuration thereof.

That is, the shape memory member layer 104 comprises a material—such as a nickel titanium alloy or Nitinol—that has a defined memory configuration from which the layer 104 can be deformed and to which the layer 104 recovers when heated to corresponding recovery temperatures.

The operation of Nitinol and other alloys which exhibit such memory or recovery from a heat unstable state is discussed in various references and is not elaborated on here. Reference is made, however, to U.S. Pat. No. 3,606,592 to Madurski et al and to U.S. Pat. No. 4,018,547 to Rogen which describe the shape memory phenomenon and are incorporated herein by reference. In brief, Nitinol has a temperature above which the memory configuration is set. By holding the Nitinol to a given shape at such temperature (e.g. approximately 900° F. for 55-Nitinol), the memory configuration becomes fixed. Nitinol also has a transition temperature range (TTR)below which the alloy is ductile and may be plastically deformed and above which recovery occurs. Raising the alloy to temperatures above the TTR, then, causes atoms of the alloy displaced during deformation to return their predeformed positions. Accordingly, Nitinol and similar alloys characterized with memory shape can be repeatedly deformed and recovered in alternation by deforming the Nitinol when below the TTR and by heating the alloy to recovery temperatures thereafter. As is known in the art, the TTR, or recovery temperatures, may be determined between −200° F. and +300° F. by proper selection of alloy. In the present instance, recovery temperatures preferably exceed typical body temperatures and the alloys employed are body compatible.

Referring again to FIG. I, the springy member layer 108 has a resilience sufficient to deform the clamp 100—including the shape memory member layer 104—at temperatures below heat recovery. When the shape memory member layer 104 is elevated in temperature above its heat recovery level, the shape memory member layer 104 recovers against the springy member layer 108 to expand the clamp 100.

When the clamp 100 is implanted about a vessel (not shown) in a living body, the contracting of the clamp 100 serves to pinch the vessel closed whereas expansion thereof enables a substance to flow through the vessel. This effect is illustrated in FIGS. II and III.

In FIGS. II and III, an artificial sphincter 200 includes a clamp 202 having a horseshoe shape. The clamp 202 comprises a plurality of coaxial layers: a spongy layer 204, a heater layer 206, a shape memory member layer 208, and a springy member layer 210. In FIG. II, the springy member layer 210 has deformed the clamp 202—including the shape memory member layer 208—to pinch a vessel 212 closed. An AC source 216, external to the living body (not shown) of which the vessel 212 is a part, is shown in FIG. II not providing any output. In FIG. III, the AC source 216 is providing power to the clamp 202 via coil 220. The AC induces a current in the heater layer 206 which transfers the heat generated therein to the shape memory member layer 208. Sufficient heat is generated to recover the shape memory member layer 208. Upon recovery of the shape memory member layer 208, the clamp 202 expands, thereby opening the vessel 212. By switching the AC source 216 on and off, the vessel 212 is respectively opened and pinched closed. Also, in the FIG. II and III embodiment as discussed, the clamp 202 automatically pinches the vessel 212 closed due to the bias of the springy member layer 210 when the shape memory member layer 208 is below recovery temperatures. The vessel 212 is opened only when sufficient power or A.C. is supplied by the source 216.

Turning now to FIGS. IV and V, a coil-shaped clamp 300 is shown. The top view shown in FIG. V shows five stacked layers 302 through 310 which are coiled concentrically and implantable about a vessel (not shown). As in the previously discussed embodiments, a spongy inner layer 302 is provided to cushion and protect the tissue about the vessel and to distribute the force thereagainst. Also, as in the previously discussed embodiments, a shape memory member layer 304, a heater layer 308, and a springy member layer 310 are provided. In addition, however, a thin electrical insulator layer 306 is interposed between the heater layer 308 and shape memory member layer 304. The insulator layer 306 is included to enhance heating—confining the induced current to the higher resistance heater layer 308.

In reviewing FIG. V, it is noted that the spongy layer 302 may be deleted if desired where force distribution and cushioning may not be required. Furthermore, the heater layer 308 and insulator layer 306 may also be deleted where the shape memory member layer 304 is directly heated by current induced therein by an AC source (not shown). In such a case, however, the impedance in just the shape memory alloy is lower than in the heater layer, and thus greater current is required to generate the desired heat. Hence, a separate heater layer 308 is preferably included. In a specific embodiment, the heater layer 308 may comprise a self-regulating heater which maintains the temperature level substantially constant. Such a heater is discussed by Carter and Krumme in U.S. Pat. No. 4,256,945 and also in a published application PCT/US82 /00303 filed March 16, 1981. The heater layer 308 may thus include one layer of magnetic material or a laminate including a magnetic layer and an electrically conductive layer wherein current is substantially confined to a thin skin at temperatures below the Curie temperature (hereafter referred to as just "Curie") of the magnetic material and to an expanded skin at temperatures above Curie where the Curie generally corresponds to the heat recovery temperatures. A self-regulating heater including a polymeric layer may also be employed.

Referring to FIG. VI, a coil-shaped clamp 400 of an artificial sphincter 402 is shown implanted in a living body 404 about a vessel 406. The clamp 400 has a multilayer coaxial cross-section including a shape memory layer 408 which surrounds a heater layer 410 which, in turn, surrounds a springy layer 412. In this embodiment—as in the FIG. IV and V embodiment—the clamp 400 can contract to pinch the vessel 406 closed and expand to open the vessel 406. In FIG. VI, however, the clamp 400 is normally held open by the springy layer 412 which deforms the shape memory layer 408 when at temperatures below recovery. When the AC source 416 induces current in layer 410 via coil 420, the shape memory layer 408 recovers to contract the clamp 400. The clamp 400 contracts enough to pinch the vessel 406 closed. To keep the vessel 406 closed, AC must be applied.

It is noted, of course, that each embodiment may provide either normally open or normally pinched closed operation by properly positioning the layers, properly flexing the springy member, and properly defining the memory configuration of the shape memory member. In FIG. I, for example, by interchanging the shape memory member layer 104 with the springy member layer 108 and by causing the shape memory member layer 104 to press inwardly upon recovery to counteract an outward bias of the springy member layer 108, a normally open vessel is provided.

Furthermore, by properly selecting the shape memory member relative to the resilience or spring force of the springy member, a desired closure characteristic can be achieved. For example, the pressure against the vessel tissue upon closure may be precisely defined as well as the speed, or slowness, with which closure is effected by deformation of the shape memory member.

In the above embodiments, the spongy inner layer is a body compatible material such as sponge urethane, silicone, foamed teflon (which has 80% to 90% void space), or sponge teflon as applicable. The springy member layer is also body compatible and may comprise hard-rolled stainless steel, Titanium, or a springy polymer. In any case, the springy member has a resilience sufficient to deform the clamp at temperatures below recovery, the shape memory member overcoming the force of the springy member at temperatures above recovery. The heater layer may include a thin Nichrome wire or foil. The AC source can be any of various commercially available sources which have sufficient power to heat the heater layer but do not cause injury to the body. AC sources, for example, which are employed in communicating with intracranial pressure monitors and implantable infusion pumps may be used in the present invention provided sufficient current is induced in the clamp.

Moreover, the invention further contemplates embodiments wherein the clamp is not necessarily curved in shape and wherein the layers need not be coextensive in their respective longitudinal, radial, or circumferential dimensions. In FIGS. II and III, for example, the clamp 202 may have a D-shaped transveral cross-section. That is, rather than a horseshoe-shaped cylinder with a circular cross-section, a horseshoe-shaped cylinder with a D-shaped cross-section is contemplated.

Further, the invention need not be limited to a structure wherein deformation is necessarily effected by a separate springy member. Specifically, it is contemplated that the vessel itself may have sufficient resilience to serve as a springy member or means to deform the shape memory member below recovery temperatures. In such a case the vessel opens by its own force and recovery of the shape memory member causes closure thereof.

Still further, the invention contemplates the use of two shape memory members—to effect opening and one to effect or enhance closure. This can be achieved by selecting alloys which recover at different temperatures and with different strengths. For example, a first shape memory member may recover at $T_1$ to contract the clamp—alone alone or in conjunction with a springy member. The temperature $T_1$ is below the recovery temperatures $T_2$ of the second shape memory member. When temperature $T_2$ is reached, the second shape memory member counteracts the first shape memory member (and springy member) to expand the clamp and open the vessel.

Also, it is not required that elements of the clamp be layers in a multilayer structure. The springy member may comprise a coil or other such spring as an alternative to a springy layer. By way of example, in FIGS. II and III, layer 210 may be replaced by a spring band encircling the two ends of the horseshoe-shaped clamp 202. As the two ends spread out and the clamp 202 expands, the spring stretches (or flexes). The spring band urges the clamp 202 back to the FIG. II configuration when heat is no longer supplied.

Finally, the springy member resilience may be selected to provide a desired pressure against vessel tissue upon closure of the vessel responsive to deformation of the shape memory member by the springy member. By employing a shape memory member to counteract the springy member, the pressure may be relatively precisely controlled.

Other improvements, modifications, and embodiments will become apparent to one of ordinary skill in the art upon review of this disclosure. Such improvements, modifications and embodiments are considered to be within the scope of this invention as defined by the following claims.

I claim:
1. An artificial sphincter comprising:
   a shape memory implantable about a substance-carrying vessel in a living body; and
   deforming for urging said shape memory member to a deformed configuration from a memory configuration thereof;
   said shape memory being heat recoverable to the memory configuration thereof after being deformed therefrom by said deforming means, and
   heater means for heating said shape memory member to heat recoverable temperatures;
   said shape memory member at least partially clamping the vessel in one of said configurations.

2. An aritifical sphincter according to claim 1 wherein said shape memory member, said deforming means, and said heater means each comprise a layer in a curved multilayer structure having a concave inner surface; and
   wherein said concave inner surface pinches the wall of the vessel closed when said shape memory member is in the memory configuration thereof; and
   wherein said concave inner surface is displaced to permit the wall of the vessel to expand when said shape memory member is deformed from the memory configuration thereof.

3. An artifical sphincter according to claim 2 further comprising:
   alternating current source means external to the living body for inducing current in the layer comprising said heater means;
   said heater means comprising a resistive heater which heats said shape memory member to heat recovery temperatures responsive to said source means inducing current therein.

4. An artificial sphincter according to claim 3 wherein said multilayer structure further comprises a layer of thermally conductive electrical insulation sandwiched between said shape memory member layer and said heater means layer.

5. An artificial sphincter according to claim 3 wherein said multilayer structure further comprises a spongy inner layer having an inner surface corresponding to said concave inner surface;
said shape memory member forming the outer layer of said multilayer structure; and
said heater means and layer of insulation forming layers interposed between said spongy inner layer and the outer layer.

6. An artificial sphincter according to claim 5 wherein said multilayer structure comprises a plurality of coaxial layers.

7. An artificial sphincter according to claim 2 wherein said multilayer structure has a U-shape which is contracted inwardly when said shape memory member is in the memory configuration thereof and which is expanded outwardly when said shape memory member is deformed from the memory configuration thereof.

8. An artificial sphincter according to claim 2 wherein said multilayer structure has a coil shape which is contracted inwardly when said shape memory member is in the memory configuration thereof and which is expanded outwardly when said shape memory member is deformed from the memory configuration thereof.

9. An artificial sphincter according to claim 2 wherein said multilayer structure further comprises a spongy inner layer having an inner surface corresponding to said concave inner surface;
said shape memory member forming the outer layer of said multilayer structure; and
said heater means forming a layer interposed between said spongy inner layer and the outer layer.

10. An artificial sphincter according to claim 3 wherein said multilayer structure comprises a plurality of coaxial layers.

11. An artificial sphincter according to claim 2 wherein said multilayer structure comprises a plurality of stacked layers.

12. An artificial sphincter according to claim 2 wherein said deforming means comprises a resilient layer which is flexed when said shape memory member layer is in the memory configuration thereof, said resilient layer unflexing to deform said shape memory member at temperatures below heat recovery temperatures.

13. An aritificial sphincter according to claim 2 further comprising:
alternating current means external to the living body for inducing current in the layer comprising said heater means.

14. An artificial sphincter comprising:
a clamp implantable about a substance-carrying vessel in a living body, said clamp comprising:
a shape memory member having a memory configuration; and
deforming means for urging said shape memory member to a deformed configuration from a memory configuration thereof;
said shape memory member being heat recoverable to the memory configuration after being deformed therefrom by said deforming means;
wherein said clamp is dimensioned to permit substance flow through the vessel when implanted and when said shape memory member is in the memory configuration thereof and wherein said clamp is dimensioned to pinch the vessel closed when implanted and when the shape memory member is deformed from the memory configuration thereof by said deforming means, and
heater means for heating said shape memory member to heat recoverable temperatures.

15. An artificial sphincter according to claim 14 wherein said shape memory member, said deforming means, and said heater means each comprise a layer in a curved multilayer structure having a concave inner surface; and
wherein said concave inner surface presses against the wall of the vessel to effect closure thereof when said shape memory member is deformed from the memory configuration thereof; and
wherein said concave inner surface is displaced to permit the wall of the vessel to open when said shape memory member is in the the memory configuration thereof.

16. An artificial sphincter according to claim 15 further comprising:
induced A.C. source means external to the living body for inducing current in the layer comprising said heater means;
said heater means comprising a resistive heater which heats said shape memory member to heat recovery temperatures responsive to said source means inducing current therein.

17. An artificial sphincter according to claim 16 wherein said multilayer structure further comprises a layer of thermally conductive electrical insulation sandwiched between said shape memory member layer and said heater means layer.

18. An artificial sphincter according to claim 17 wherein said multilayer structure further comprises a spongy inner layer having an inner surface corresponding to said concave inner surface;
said shape memory member forming the outer layer of said multilayer structure; and
said heater means and layer of insulation forming layers interposed between said spongy inner layer and the outer layer.

19. An artificial sphincter according to claim 15 wherein said multilayer structure has a U-shape which is contracted inwardly when said shape memory member is deformed from the memory configuration thereof and which is expanded outwardly when said shape memory member is in the memory configuration thereof.

20. An artificial sphincter according to claim 15 wherein said multilayer structure has a coil shape which is contracted inwardly when said shape memory member is deformed from the memory configuratiin thereof and which is expanded outwardly when said shape memory member is in the memory configuration thereof.

21. An artificial sphincter according to claim 15 wherein said multilayer structure further comprises a spongy inner layer having an inner surface corresponding to said concave inner surface;
said shape memory member forming the outer layer of said multilayer structure; and
said heater means forming a layer interposed between said spongy inner layer and the outer layer.

22. An artificial sphincter according to claim 15 wherein said deforming means comprises a resilient layer which is flexed when said shape memory member layer is in the memory configuration thereof, said resilient layer unflexing to deform said shape memory member at temperatures below heat recovery temperatures.

23. A method of selectively clamping a vessel in a living body closed including the steps of:
  implanting a shape memory member at least partially about the vessel;
  selectively expanding and contracting the implanted shape memory member to respectively open and close the vessel to the flow of substance therethrough;
  said selective expanding and contracting including the steps of selectively (a) deforming the shape memory member from a memory configuration thereof and (b) heat recovering the shape memory member to the memory configuration thereof.

24. A method according to claim 23 wherein said expanding corresponds to said deforming step and wherein said contracting corresponds to said heat recovering step.

25. A method according to claim 24 wherein said contracting corresponds to said deforming step and wherein said expanding corresponds to said heat recovering step.

26. A method according to claim 23 wherein said implanting step includes the step of coiling the shape memory member about the vessel.

27. A method according to claim 23 wherein said selective expanding and contracting step further includes the step of:
  repetitively controllably expanding and contracting the implanted shape memory member.

28. An artificial sphincter comprising:
  a clamp disposed about a vessel in a living body, said clamp including:
    a spring member biasing said clamp to pinch the vessel closed; and
    a shape memory recoverable to a memory configuration when heated to recovery tempertures;
  wherein said shape memory member opposes the vessel closing bias of said spring member to enable the vessel to pass a substance therethrough responsive to recovery of said shape memory member to the memory configuration thereof, and
  means, external to the body, for non-invasively heating said shape memory member to recovery temperatures.

29. An artifical sphincter according to claim 28 further comprising:
  a heater layer which transfers heat to said shape memory member in response to current flow through said heater layer; and
  coil means, connected to said heater layer, for picking up induced A.C. power transmitted thereto and providing current to said heater layer in response to said coil means picking up A.C. power.

30. An artificial sphincter comprising:
  a shape memory member implatable about a substance carrying vessel in a living body;
  deforming means for urging said shape memory member to a deformed configuration from a memory configuration thereof;
  said shape memory member changing its configuration after being deformed upon a change of temperature thereof;
  wherein said shape memory member is dimensioned to clamp the vessel in one of said configurations and to permitting substance to flow through the vessel in the other of said configurations, and
  means for changing the temperature of said shape memory member.

* * * * *

UNITED STATES PATENT AND TRADEMARK OFFICE
CERTIFICATE OF CORRECTION

PATENT NO. : 4,556,050
DATED : December 3, 1985
INVENTOR(S) : Darel E. Hodgson, et al.

It is certified that error appears in the above-indentified patent and that said Letters Patent is hereby corrected as shown below:

Column 1, line 23, delete "Reincke" and insert --Reinicke--; therefore

Line 27, after "sphincter" insert --. First, in many applications, the artificial sphincter--; therefore Line 66, after "closed.", new paragraph, insert --Preferably, the shape memory member is heated--; therefore Column 4, lines 66-67, delete "embodimen-t--" and insert --embodiment--as--; therefore Column 5, line 66, after "members--" insert --one--; therefore Column 6, line 3, after "clamp--" delete "alone"; therefore Line 36, after "memory" insert --member--; therefore Line 38, after "deforming" insert --means--; therefore Line 41, after "memory" insert --member--; therefore Column 7, line 44, after "claim" delete ":"; therefore Column 10, line 1, after "member" insert --for--; therefore Line 3, after "memory" insert --member--.

Signed and Sealed this

Twenty-third Day of May, 1995

Attest:

BRUCE LEHMAN

Attesting Officer

Commissioner of Patents and Trademarks